(12) United States Patent
Malowaniec

(10) Patent No.: US 6,414,216 B1
(45) Date of Patent: Jul. 2, 2002

(54) ABSORBENT SINGLE USE HYGIENE ITEM

(75) Inventor: Krzysztof Daniel Malowaniec, Heidenheim (DE)

(73) Assignee: Paul Hartmann AG, Heidenheim (DE)

(*) Notice: Subject to any disclaimer, the term of this patent is extended or adjusted under 35 U.S.C. 154(b) by 0 days.

(21) Appl. No.: 09/463,562

(22) PCT Filed: Jul. 28, 1998

(86) PCT No.: PCT/EP98/04702
§ 371 (c)(1),
(2), (4) Date: Jan. 27, 2000

(87) PCT Pub. No.: WO99/05999
PCT Pub. Date: Feb. 11, 1999

(30) Foreign Application Priority Data

Jul. 29, 1997 (DE) .......................... 197 32 550

(51) Int. Cl.[7] ................................ A61F 13/15
(52) U.S. Cl. ............... 604/378; 604/370; 604/368; 604/367; 604/358; 604/374
(58) Field of Search ............... 604/378, 370, 604/368

(56) References Cited

U.S. PATENT DOCUMENTS

| | | | | |
|---|---|---|---|---|
| 4,798,603 A | * | 1/1989 | Meyer | 604/378 |
| 5,294,478 A | * | 3/1994 | Wanek | 428/218 |
| 5,300,054 A | * | 4/1994 | Feist | 604/378 |
| 5,601,542 A | * | 2/1997 | Melius | 604/368 |
| 5,653,702 A | * | 8/1997 | Brohammer | 604/370 |
| 6,020,536 A | * | 2/2000 | Osterdahl | 604/378 |

FOREIGN PATENT DOCUMENTS

| | | | | |
|---|---|---|---|---|
| DE | OS 43 38 326 | | 5/1995 | |
| DE | 88 17 262 | | 5/1996 | |
| DE | 92 18 991 | | 10/1996 | |
| DK | 4338326 A1 | * | 5/1995 | A61F/13/15 |
| DK | 8817262 U1 | * | 5/1996 | A61F/13/46 |
| DK | 9218991 U1 | * | 10/1996 | A61F/13/46 |
| EP | 0 151 018 | | 8/1985 | |
| EP | 0 151018 A2 | * | 8/1985 | A61F/13/18 |
| EP | 0 689818 A2 | * | 1/1996 | 604/358 |
| EP | 0 689 818 | | 1/1996 | |
| GB | 2 296438 A | * | 7/1996 | A61F/13/15 |
| GB | 2 296 438 | | 7/1996 | |
| WO | WO 9211830 | * | 7/1992 | A61F/13/46 |
| WO | WO 9414397 | * | 7/1994 | A61F/13/15 |
| WO | WO 95 10996 | * | 4/1995 | A61F/13/46 |
| WO | WO 9710789 | * | 3/1997 | A61F/13/15 |

* cited by examiner

Primary Examiner—Amy Vanatta
Assistant Examiner—Angela J. Grayson
(74) Attorney, Agent, or Firm—Paul Vincent

(57) ABSTRACT

The invention concerns an absorbent single use hygiene item comprising a liquid-tight back sheet (4) and a liquid permeable cover sheet (2), with an absorbent body (6) containing super-absorbent polymer materials and suitable for storing bodily fluids, especially urine, which is disposed between the back sheet (4) and the cover sheet (2), and with a two-ply intermediate layer (8) which takes up and distributes liquid. The intermediate layer (8) is made from a top stratum (18) consisting of synthetic fibers and a bottom stratum (20), the average pore volume of the top stratum (18) being greater than the average pore volume of the bottom stratum (20), and is disposed between the absorbent body (6) and the cover sheet (2). The hygiene item in accordance with the invention is constructed in such a fashion that the bottom stratum (20) consists essentially of chemically cross-linked cellulose fibers and the longitudinal end sections (19) the top stratum (18) overlap the longitudinal ends (21) of the bottom stratum (20) so that the hygiene item can absorb repeated liquid discharge and gives the wearer a feeling of dryness. The cross-linked cellulose fibers of the bottom stratum (20) are also more hydrophilic than the synthetic fibers of the top stratum (18).

14 Claims, 1 Drawing Sheet

ABSORBENT SINGLE USE HYGIENE ITEM

BACKGROUND OF THE INVENTION

Figure 2:
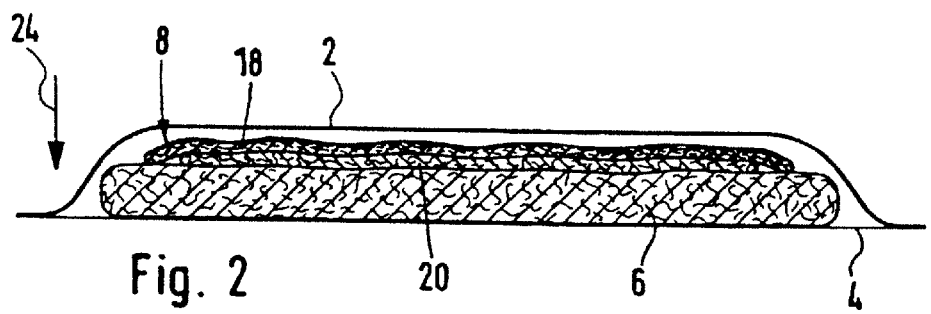

The invention concerns an absorbent single use hygiene item having a liquid tight back sheet, a liquid permeable cover sheet, an absorbent body comprising a suitable super absorbing polymer material (SAP material) disposed between the cover and the back for absorbing body fluids, in particular urine, and with a liquid absorbing intermediate layer comprising a top stratum (18) made from synthetic fibers and a bottom stratum (20), wherein the average pore volume of the top stratum (18) is larger than the average pore volume of the intermediate layer (8) bottom stratum (20) and wherein the intermediate layer (8) is disposed between the absorbent body (6) and the cover sheet (2).

A hygiene item of this kind has been disclosed in DE 92 18 991 U1. EP 0 689 818 A2 discloses a hygiene item with which the intermediate layer is manufactured together with the absorbent layer using a multi-layer flat material comprising a liquid tight back sheet, a cover sheet which is permeable to liquids, and an absorbent body containing a super-absorbent polymer material and disposed between the sheets which is suitable for the storage of body liquids, in particular urine. A two-ply liquid absorbing and distributing intermediate layer consists essentially of a top stratum made from synthetic fibers and a bottom stratum, wherein the average pore volume of the top stratum is larger than the average pore volume of the bottom stratum. The intermediate layer is disposed between the absorbent body and the cover sheet.

Hygiene items, in particular diapers or incontinence inlays, containing SAP materials in their absorbent body are susceptible to so-called gel blocking. The SAP materials swell in the region of liquid discharge to impair additional liquid acceptance in particular in response to repeated liquid discharge in these regions. The intermediate layer disposed between the cover sheet and the absorbent body is thereby intended to act as a kind of intermediate buffer for absorbing the incident liquid, for distributing the liquid within intermediate layer, and for passing the liquid into the absorbent body. Liquids in the vicinity of liquid discharge can thereby be transported to remote locations of the absorbent body or to SAP materials contained therein which are still present in an "unused" state.

WO 91/11162 discloses a hygiene item having a liquid acceptance and distribution layer located above the absorbent body and comprising cross-linked cellulose fibers.

The chemical cross-linkage of the cellulose molecules is present within the cellulose fibers through cross-linkage of the cellulose molecules within a single fiber only and is not active between fibers. In consequence thereof, these fibers are relatively stiff, textured, and elastic. The intramolecular absorption capacity of the fibers is reduced. Such fibers are better suited for processing repeated discharge of liquid streams than are the non-chemically cross-linked cellulose fibers of the absorbent body. They are better suited for rapid absorption, containment, internal distribution and passage thereof to the absorbent body. In addition to the chemically cross-linked cellulose fibers, the intermediate layer of the conventional hygiene item contains a thermoplastic bonding material in the form of an admixture of thermoplastic fibers. Heating of the fiber mixture leads to melting of the thermoplastic fibers and to glue-like mutual bonding and securing of the chemically cross-linked cellulose fibers. This is reported as being particularly advantageous.

EP 0 397 110 A1 describes a diaper having a synthetic fiber-based, voluminous bonded fiber fabric which is disposed as an intermediate layer between the absorbent body and the cover sheet to provide temporary liquid absorption. The layer must however have an area density of at least 60 $g/m^2$ for adequate intermediate storage and distribution of the discharged liquid. Materials used in the voluminous, bonded fiber fabric layer are expensive, create logistic problems, and are difficult to integrate into high speed machinery, since a continuous roll of this material having finite, conventional usable diameter can only have a very limited working length and frequent exchange of the rolls is necessary.

Departing from the above described prior art, it is the underlying purpose of the invention to create a hygiene item having a high fraction of super-absorbing polymer materials in the absorbent body whose storage capacity can be better and more completely used than that of the hygiene article disclosed in WO 91/11162. In addition, the hygiene item must be inexpensive to produce. Departing from the hygiene item categorizing the invention, it is the underlying purpose of the present invention to create a hygiene item of simple construction which is therefore inexpensive to manufacture, whose liquid absorption performance and whose liquid storage performance is improved, in particular, in response to repeated application of liquids. The hygiene item user should also not feel the liquid remaining in the intermediate layer, e.g. as a result of body weight pressure on the skin following repeated liquid discharge.

SUMMARY OF THE INVENTION

This purpose is achieved in accordance with the invention with a hygiene item of the above mentioned kind, wherein the bottom stratum is made from chemically cross-linked cellulose fibers and the longitudinal end sections of the top stratum overlap the longitudinal ends of the bottom stratum, with the hydrophilicity of the chemically cross-linked cellulose fibers of the bottom stratum being larger than that of the synthetic fibers of the top stratum.

In accordance with the invention, the lower stratum of the intermediate layer is made solely from chemically cross-linked cellulose fibers. The good performance of the two stratum intermediate layer constructed in accordance with the invention results from a synergetic interaction which can be explained as follows. The gradient of the average pore volume (as seen in a direction towards the absorbent body, perpendicular to the plane of the cover sheet) initially provides a relatively large-pored liquid acceptance volume for liquids incident on the top stratum of the intermediate layer. The liquid can then gain access into the absorbent body via the bottom stratum of the intermediate layer. The reduced hydrophilicity of the synthetic fibers in the top stratum of the intermediate layer compared to that of the chemically cross-linked cellulose fibers of the bottom stratum of the intermediate layer and, in addition, its preferentially lower hydrophilicity compared to the non-cross-linked cellulose fibers of the absorbent body, support the desired direction of liquid transport. The bottom stratum of the intermediate layer made from chemically cross-linked cellulose fibers has a certain liquid guidance capacity due to the capillary absorption action of the fibers so that liquids passing through the top stratum of the intermediate layer and into the bottom stratum are distributed through the plane thereof into regions removed from the point of liquid incidence for further transport into the underlying absorbent body at these locations. Following repeated discharge of liquids, the storage capacity of the absorbent body is nevertheless nearly exhausted in the regions at which liquids are incident. This point in time is critical for the function of the hygiene item. The bottom stratum of the intermediate storage layer can then store additional incident liquid, at least to a limited extent. This storage capacity is effected by the remaining molecular bonding capacity of the cross-linked fibers and by the pore volume remaining between the fibers. The bottom stratum of the intermediate layer thereby provides reserve storage capacity. The amount of liquid stored therein which is pressed out to the surface of the diaper, i.e. to the skin of the diaper user, is thereby substantially reduced, since the upper large pore stratum of the intermediate storage layer has synthetic fibers with reduced hydrophilicity and therefore functions as a spacer. The synthetic fibers of the top stratum of the intermediate layer preferentially have very reduced hydrophilicity and therefore do not allow for substantial molecular bonding of liquids. This layer therefore remains essentially dry.

The overlap of the longitudinal end sections of the top stratum of the intermediate layer with the longitudinal ends of the bottom stratum of the intermediate layer reliably prevents liquids which may be present in the bottom stratum of the intermediate layer from being pushed to the surface of the hygiene item.

The edges of the longitudinal end sections of the top stratum advantageously lie within the absorbent body, i.e. at a separation from the longitudinal ends. The storage capacity of the absorbent body can thereby be better utilized. For the above mentioned case of repeated liquid discharge, the storage capacity of the absorbent body is exhausted in the region of incidence thereof and the bottom stratum of the intermediate storage layer assumes its reserve storage function to transport additional incident liquid at the border between the two strata of the intermediate storage layer or in the lower region of the upper stratum of the intermediate storage layer. The liquid is reliably passed into the absorbent body when it reaches the longitudinal ends of the bottom stratum of the intermediate layer, assuming that the storage capacity of the absorbent body has not yet been exhausted in this region.

In accordance with a preferred embodiment, the above mentioned liquid transport in the lower region of the top stratum of the intermediate layer can be improved when the top stratum has a pore volume which decreases in the direction of liquid transport from the cover sheet to the absorbent body, i.e. perpendicular to the plane of the layer. The pore volume must not decrease in a discrete manner from a larger value to a smaller value, rather can decrease in a quasi-continuous fashion in a downward direction within the top stratum of the intermediate layer.

The intermediate layer is preferentially constructed in such a fashion that the fibers of the top stratum engage into the bottom stratum to thereby form a transitional zone between the strata. The fibers in the bottom stratum can correspondingly engage into the absorbent body so that a transitional zone is also formed between the intermediate layer and the absorbent body.

The above described two-ply construction for the intermediate layer and the function of the bottom stratum thereof facilitate a low surface density for the top stratum, preferentially less than 55 g/m². This permits preparation of a continuous roll of materials used therefor having, from a manufacturing point of view, a satisfactory, large working length so that the material can be integrated into high speed manufacturing equipment.

The top stratum of the intermediate layer is preferentially made from a bonded fiber fabric which is more voluminous than the bonded fiber fabric of the cover sheet. A large number of conventional synthetic fibers are known to one of average skill in the art as are methods for the manufacture of bonded fiber fabrics and further description thereof is unnecessary. The bonded fiber fabric preferentially comprises conventional two-component fibers e.g. of the cladded core type. A fiber fabric can thereby be conventionally, thermally processed into a consolidated bonded fiber fabric without damaging the fiber structure. Two-component fiber thicknesses of at least 4 dtex and preferentially between 5 to 8 dtex have turned out to be advantageous. In this manner, the titer of the fibers is sufficiently large to give the bonded fiber fabric the desired pore volume, even following thermal compacting. (Thick fibers cannot be packed and volume-filled to the same extent as thin fibers). One of average skill in the art is also aware of means for adjusting the hydrophilicity of synthetic fibers so that further discussion thereof is not needed here. Using such techniques, the preferentially very low hydrophilicity of the top stratum of the intermediate layer can be substantially reduced to, in any event, be significantly lower than that of the chemically cross-linked fibers of the bottom stratum. The absorbent body below the intermediate layer is advantageously double-layered, with the upper layer thereof substantially containing cellulose fibers and super-absorbing polymer materials and the lower layer consisting essentially of cellulose fibers only. An optimized use of the absorption capacity of the absorbent body is thereby effected.

Further advantages, details and features of the invention can be derived from the accompanying patent claims and drawings as well as from the subsequent description of a preferred embodiment of the invention.

BRIEF DESCRIPTIONS OF THE DRAWINGS

Figure 1:
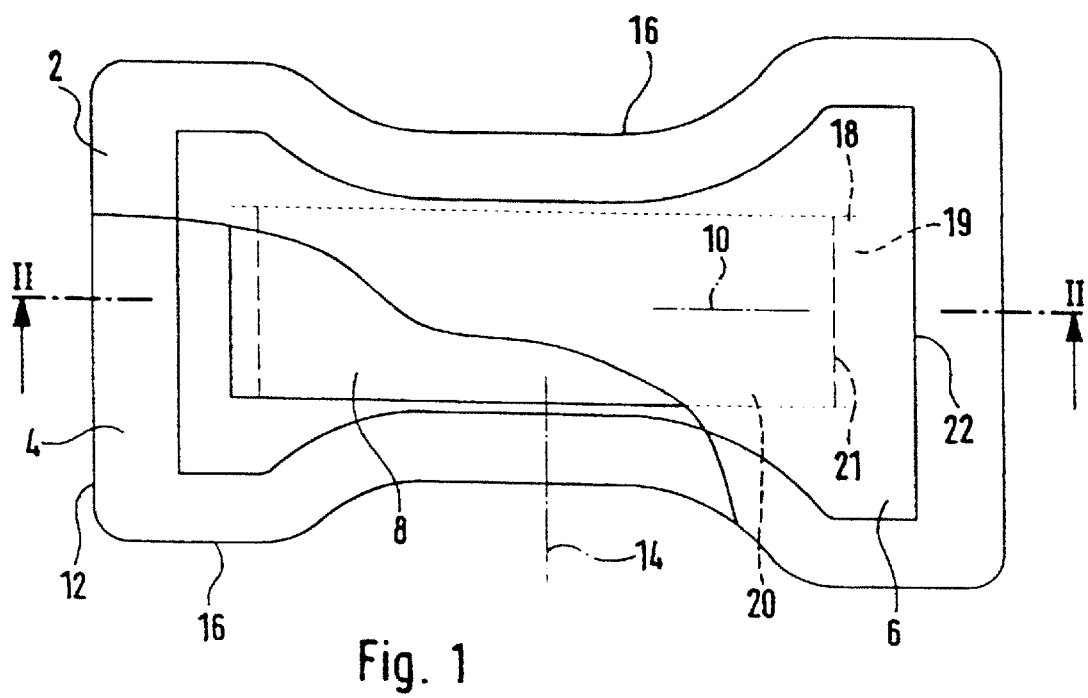

FIG. 1 shows a schematic view of the structure of a hygiene item in accordance with the invention, and FIG. 2 shows a longitudinal cut in the plane designated by the arrows II—II.

DESCRIPTION OF THE PREFERRED EMBODIMENT

The figures schematically show the structure of a hygiene item in the embodiment of a diaper. The diaper comprises a cover sheet 2, a liquid tight back sheet 4 and an intermediate absorbent body 6. A two stratum intermediate layer (designated in its entirety with reference symbol 8) is disposed between the cover sheet 2 and the absorbent body 6. In the embodiment shown, the cover sheet 2 extends in a longitudinal direction 10 of the diaper to longitudinal edges 12 thereof and, in the transverse direction 14, up to the sideward transverse edges 16 of the diaper. The liquid permeable cover sheet 2 is connected to the back sheet 4 along and proximate to the longitudinal edges 12 and the transverse edges 16 using arbitrarily conventional joining techniques. An embodiment is also conceivable with which the cover sheet 2 ends at a separation from the transverse edges 16. Additional e.g. bundling elements or stretching means can then be disposed past the cover sheet 2.

The two-ply intermediate layer 8 comprises a top stratum 18 and a bottom stratum 20. In the longitudinal direction 10, the longitudinal end sections 19 of the top stratum 18 overlap the longitudinal ends 21 of the bottom stratum 20 but end at or at a separation from the longitudinal ends 22 of the absorbent body 6. The top and bottom strata 18 and 20 have the same width in the transverse direction 14. The top stratum 18 can also advantageously overlap with the bottom stratum 20 in the transverse direction.

The top stratum 18 is formed from a bonded fiber fabric made from synthetic fibers. A fraction of two-component fibers is preferentially used therefor. The bonded fiber fabric is compressed during manufacture in such a fashion that the top stratum 18 has a pore volume which decreases in the direction of arrow 24 of FIG. 2, i.e. in the direction of liquid transport, transverse to the planar extension of the intermediate layer 8.

The bottom stratum 20 consists essentially of chemically cross-linked cellulose fibers. The pore volume of the bottom stratum 20 is lower than that of the top stratum 18 of the intermediate layer 8. The hydrophilicity of the chemically cross-linked cellulose fibers of the bottom stratum 20 is also larger than that of the synthetic fibers in the bonded fiber fabric constituting the top stratum 18.

When the liquid acceptance capacity of the absorbent body 6 is exhausted in the region of liquid discharge following large amounts of incident liquid, the intermediate layer 8 assumes a liquid storage and transport function. Renewed streams of liquid are briefly absorbed in the relatively large pored volume of the top stratum 18 and then passed to the bottom stratum 20 of the intermediate layer 8, wherein the intermediate layer 8 thereby performs a storage function. When the storage capacity of the bottom stratum 20 is also exhausted, liquid transport occurs in the plane of flat extension of the strata at the border region between the top stratum 18 and the bottom stratum 20. Liquid is thereby transported away from its location of incidence and passed to non-exhausted portions of the absorbent body 6 still having remaining storage capacity.

I claim:

1. A single use absorbent hygiene article comprising:
   a liquid-tight back sheet;
   a cover sheet permeable to liquids;
   an absorbent body disposed between said back sheet and said cover sheet, said absorbent body containing a super-absorbent polymer for absorbing at least one of body liquids and urine;
   a top layer disposed between said absorbent body and said cover sheet, said top layer containing synthetic fibers and having a first average pore volume and a first average hydrophilicity; and
   an intermediate layer disposed between said top layer and said absorbent body, said intermediate layer consisting essentially of chemically cross-linked cellulose fibers and having a second average pore volume which is smaller than said first average pore volume and a second average hydrophilicity which is greater than said first average hydrophilicity, wherein said top layer has longitudinal end portions which extend past edges of said intermediate layer to directly contact said absorbent body.

2. The hygiene item of claim 1, wherein said longitudinal end portions of said top layer contact said absorbent body at a defined separation from longitudinal ends of said absorbent body.

3. The hygiene item of claim 1, wherein said top layer is made from a bonded fiber fabric containing two component fibers.

4. The hygiene item of claim 3, wherein said two-component fibers have a fiber thickness of between 5 to 8 dtex.

5. The hygiene item of claims 3, wherein said two-component fibers have a fiber thickness of at least 4 dtex.

6. The hygiene item of claim 1, wherein said top layer has a mass per unit area of less than 55 $g/m^2$.

7. The hygiene item of claim 3, wherein said top layer has a mass per unit area of less than 55 $g/m^2$.

8. The hygiene item of claim 1, wherein said intermediate layer contains no SAP material.

9. The hygiene item of claim 1, wherein said second average pore volume is larger than a third average pore volume of said absorbent body.

10. The hygiene item of claim 1, wherein said first average pore volume decreases in a perpendicular direction towards said intermediate layer.

11. The hygiene item of claim 10, wherein said top layer has an upper portion and a lower portion, wherein a pore volume of said upper portion is larger than a pore volume of said lower portion.

12. The hygiene of claim 1, wherein fibers of said top layer engage into said intermediate layer to form a first transitional zone between said top layer and said intermediate layer.

13. The hygiene item of claim 1, wherein fibers of said intermediate layer engage into said absorbent body to form a second transitional zone between said intermediate layer and said absorbent body.

14. The hygiene item of claim 1, wherein said absorbent body comprises an upper portion consisting essentially of cellulose fibers and super-absorbing polymer and a lower portion consisting essentially of cellulose fibers only.

* * * * *